US00PP09398P

United States Patent [19]

Berry

[11] Patent Number: Plant 9,398

[45] Date of Patent: Dec. 12, 1995

[54] RAPHIOLEPIS INDICA VARIETY NAMED 'CONOR'

[75] Inventor: James B. Berry, Daphne, Ala.

[73] Assignee: Flowerwood Nursery Inc., Loxley, Ala.

[21] Appl. No.: 386,756

[22] Filed: Feb. 10, 1995

[51] Int. Cl.[6] ..... A01H 5/00

[52] U.S. Cl. ..... Plt./67.5

[58] Field of Search ..... Plt./67.5

*Primary Examiner*—James R. Feyrer

[57] ABSTRACT

A new distinct variety of *Raphiolepis indica* found as an openly pollinated seedling of *Raphiolepis indica* 'Jack Evans'. The new variety is distinct with its thick leathery upturned leaves with revolute margins, bronze new growth, dense and mounding growth hibit, pink semi-double flowers, improved cold hardiness, and increased resistance to leaf spot and fireblight.

2 Drawing Sheets

BACKGROUND OF THE INVENTION

This new variety of *Raphiolepis indica* was found as an openly pollinated seedling of *Raphiolepis indica* 'Jack Evans', an unpatented variety, maintained in the Flowerwood Nursery at Kelly Road, Loxley, Ala. The seedling was found in May, 1987. The new and distinct *Raphiolepis indica* plant of this invention comprises a novel and valuable plant of dense, compact mounding habit, an abundance of pink flower clusters, attractive leaf shape, improved winter hardiness, and improved resistance to fireblight and leaf spot. The new variety has retained many of the outstanding attributes of its parent, in particular its tolerance of heat, drought, salt, insect, and disease which makes it adaptable to culture in most of the Sunbelt States. As with the parent plant, the plant of this invention, which has been named 'Conor', may be advantageously employed as a specimen appointment, a ground cover, in either formal or informal groupings, and is quite attractive in mass plantings. 'Conor' serves well in foundation plantings and is adapted for culture as a potted plant. 'Conor' is responsive to pruning and training and may be employed in forming dense, attractive hedges, and maintained without an excessive amount of care. This plant is easy to care for and maintain in size due to its short internodes, slow to moderate growth rate, heavy branching, and dense canopy. Its natural propensity to remain small to maturity makes it valuable for landscape uses in smaller home gardens which require plants which do not outgrow their intended mature dimensions.

While evaluating the *Raphiolepis indica* 'Jack Evans' seedlings, attention was directed toward leaf spot and fireblight resistance. Any of the seedlings which showed susceptibility to either disease were discarded. Most varieties of pink Raphiolepis tend to be susceptible to leaf spot and fireblight; however, this new variety was selected for its resistance to these diseases. As a result little or no chemical spray is needed which benefits the environment.

Cold hardiness was also a very important criterion. Plants of this seed group, as well as the parent, were evaluated in Alabama, Georgia, Florida, and Washington, D.C. during the winters of 1991 and 1992. The new variety, *Raphiolepis indica* 'Conor' attained high levels of cold hardiness earlier than the other selections and maintained this level of cold hardiness through the winter and into the early spring.

Asexual propagation of the new plant by cuttings has been under Mr. Berry's direction at Flowerwood Nursery in Loxley, Ala. The increased number of plants were evaluated and demonstrated stabilty of the new characteristics from generation to generation. The plant cannot be reproduced true from seed.

SUMMARY OF THE INVENTION

The following are the most outstanding and distinguishing characteristics of this new cultivar when grown under normal horticultural practices in Loxley, Ala.

1. Dense and mounding in nature. Plant is wider than tall.
2. Moderate to slow growth rate.
3. New growth terminals are pronounced with a light bronze coloration which offers a novel and strikingly appealing contrast of new foliage to old foliage in plants of this market class.
4. Hardy to Zone 7.
5. Heat and drought tolerant.
6. Good plant for coastal areas because of wind and salt tolerance.
7. Has shown good resistance to leaf spot and fireblight.
8. Relatively pest resistant.
9. Very desirable in planters.
10. Produces seeds and therefore may result in bird visitations.
11. Mature leaves are coriaceous, undulate, slightly upturned, and have a distinct revolute margin.
12. Flowers are semi-double, pink, fragrant, and profuse.

DESCRIPTION OF THE DRAWING

This new variety of *Raphiolepis indica* is illustrated by the accompanying photographic prints in which.

1.

Figure 1:
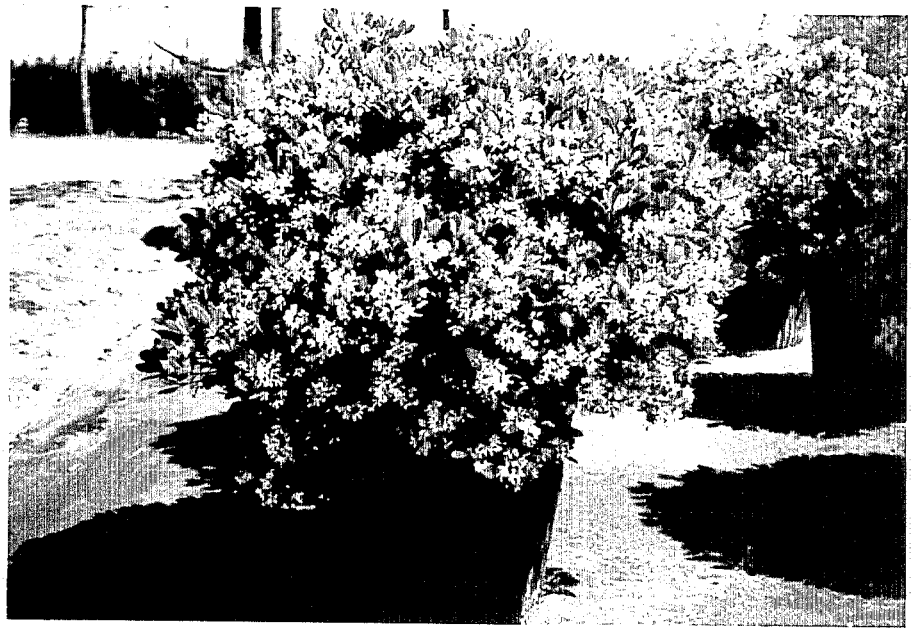
FIG. 1 discloses the dense and mounding growth habit and abundance of pink flowers of the new variety.
2.
Figure 2:
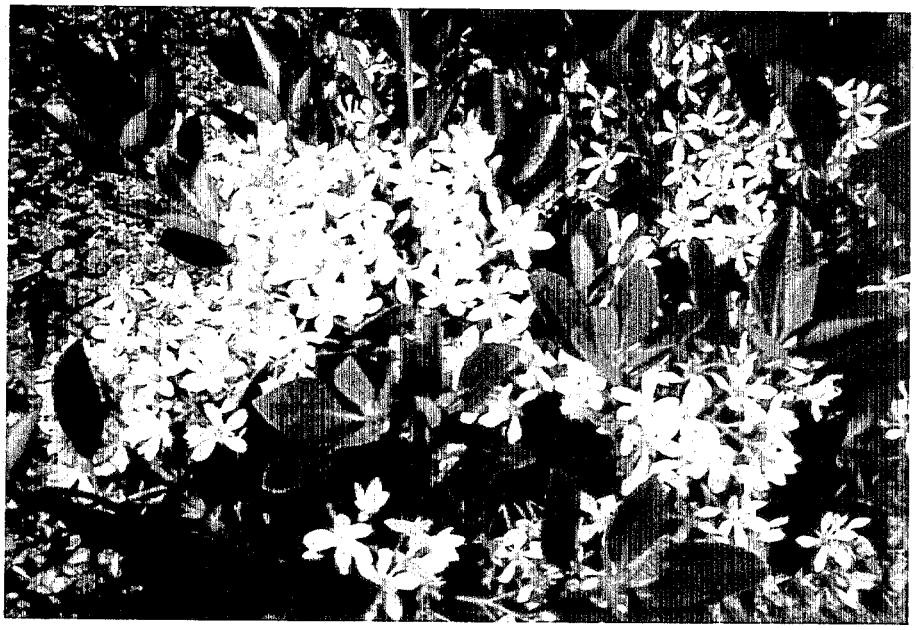
FIG. 2 is a close-up of the flowers, the almost flat immature leaves, and the light bronze coloration of the new growth.
3.
Figure 3:
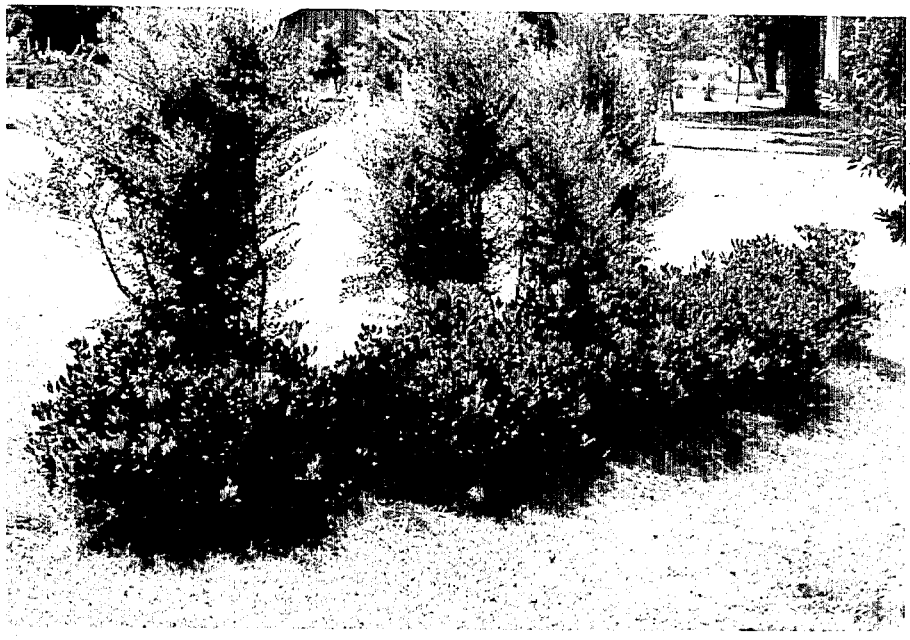
FIG. 3 shows the effective use and nature of use of the new variety in an established landscape planting.
4.
Figure 4:
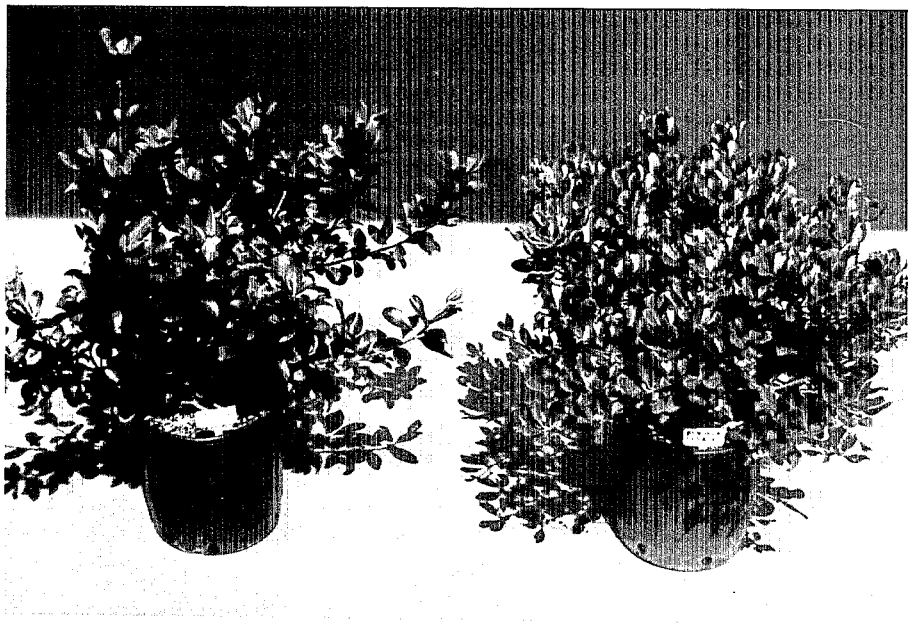
FIG. 4 is a side-by-side photograph of the parent variety *Raphiolepis indica* "Jack Evans" (on the left) and the new variety (on the right). This photograph, which was taken in late summer, shows the densely branched habit of the new variety and the unusual upturned leaves with revolute margins of the mature leaves.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Raphioleipis indica* based on my observations made of plants grown in wholesale commercial production practices, in greenhouses, and established landscape plantings in Loxley, Ala.

| | Distinctive Characteristics: | | |
|---|---|---|---|
| Characteristic | 'Conor' | 'Jack Evans' | 'Ballerina' |
| Height (Mature) | 3–4' | 4–5' | 3' |
| Width (Mature) | 4–5' | 4' | 4'+ |
| Leaf Length | 2–3" | 2–3" | 2–3" |
| Leaf Width | 1–1¼" | 1–1½" | 1–1¼" |
| Leaf Shape | elliptic-obovate | elliptic-obovate | obovate-oblanceolate |
| Leaf Margin | serrate-crenate | entire | entire |
| Leaf Tip | acute | obtuse | acute |
| Leaf curviture | undulate with revolute margins | reflexed tip | upper ½ undulate |
| Flower | Semi-double | Single | Single |
| Flower Color | Red-Purple Group 65B | Red-Purple Group 62B | Red-Purple Group 67D |
| Petal Number | 5–8 | 5 | 5 |
| Petal Shape | oblanceolate | elliptical | obovate |

The plant from which all above varieties originated has the botanical name Rosaceae *Raphiolepis indica.* The author of the genus name Raphiolepis is John Lindley (1799–1865). The original author of the species name Indica is Carlolus Linnaeus (1707–1778) and the name was transferred to the plant *Raphiolepis indica* by John Lindley.

It is from the seedlings of the *Raphiolepis indica* 'Jack Evans' plant that I found the new plant. This new variety will be sold under the trademark name Eleanor Tabor. It will be listed *Raphiolepis indica* Eleanor Tabor™ 'Conor'.

*Raphiolepis indica* 'Ballerina' U.S. Plant Pat. No. 2,972 was patented by Bordier's Nursery in 1970. It is comparable to the new plant in that both are selected seedlings of *Raphiolepis indica* 'Jack Evans' and both have a compact mounding growth habit. However there are many differences. The new plant has serrate to crenate leaf margins which are revolute compared to the entire leaf margin and undulate leaf curvature of 'Ballerina'. The flower of the new variety is semi-double and light pink compared to the 'Ballerina' flower which is single and dark pink. There is also a difference in petal shape; the new variety is oblanceolate whereas 'Ballerina' is obovate.

Classification:

*Botanic.—Raphiolepis indica* 'Conor'.

Form: Compact and mounding.

Texture: Medium to coarse.

Size: In a period of six years from a rooted cutting the plant reaches a height of 3 feet and spread of 4 feet. The plant normally grows at the rate of about 6 inches or more per year and reaches a height of 4 feet and spread of 5 feet at maturity while maintaining a dense habit due to the abundant branch development.

Growth habit: Compact, mounding evergreen shrub. Moderate to slow growth rate under normal fertilization and moisture conditions.

Foliage: Alternate, simple, evergreen, elliptic to slightly obovate, and vary in size from 2–3" long and 1–1¼" wide. The margins are serrate to crenate, with a petiole ⅜–¾" long. The midrib is prominent on both sides of the leaf and the smaller veins are prominent on the underside. Veins are depressed on the upper side giving a leathery appearance. The base of the leaf is attenuate to cuneate and the apex is acute. The upper surface of the mature leaf is Yellow-Green Group 147A, glossy, and glabrous. The underside is Yellow-Green Group 146C and matte. The underside veins are Yellow-Green Group 146A. These mature leaf colors are persistant throughout the winter. The immature leaves are tomentulose, noticeably pigmented, and are Greyed-Orange Group 166D. The paired foliaceous stipules are 3/16–⅜" and 1/16– ⅛" wide. The upper surface is Yellow-Green Group 145A and the underside is Yellow-Green Group 145B. The stipules are caducous.

The mature leaf of this new variety has an undulate shape compared to the parent plant whose leaf curls slightly under from the apex toward the base (leaf tip is reflexed). The undulate shape is common in several varieties of Raphiolepis, however, this new variety has an attractive and unique revolute margin. In addition, the leaves at the branch tips are held upward and appear whorled, similar to *Pittosporum tobira.* This undulate leaf shape with revolute margins and whorled appearance adds greatly to the attractiveness of the new variety.

In 1993, the date of initial Spring growth was March 2, in Loxley, Ala. After the initial Spring flush there was almost continuous slow growth until Fall ending October 28, also in Loxley, Ala. This growth pattern was indentical to the parent plant. When grown in full sun, the internode length of this plant and the parent plant is ½–¾". When grown in light shade the internode length is ⅝–1". As would be expected either plant grown in shade results in a taller less dense plant with larger leaves.

Stems: The young shoots have a reddish pigmentation, Greyed-Purple Group 183B, and are tomentulose. The base of the immature petioles are also Greyed-Purple Group 183B. After one of more years the stems are generally grey, Greyed-Green Group 197B, glabrous and rugose. The pith is solid and uniform.

Flowers: Perfect, semi-double, pink, Red-Purple Group 65B, ⅝" diameter, fragrant, borne on dense, upright, tomentulose, 3–4" high and wide terminal panicles from March to April. Each panicle has from 3–6 racemes which have from 1–6 flowers each, resulting in 30 or more flowers per panicle. A mature plant can have 100 or more panicles. The flowers are attached to short pedicels which are 5/16" to ½" in length. The peduncle of each raceme is from ¼" to ½" long. Each flower has 5–8 petals that are ½" long and 5/16" wide, oblanceolate, and have acute tips. The flower has from 15 to 20 stamen, ¼" long, with anthers Yellow Group 9B. The pistil consists of 2 styles which are fused at the base or ovary. There are 5 sepals, Green Group 144B, which are united and have ciliate margins. In 1993 the blooming period began March 10, in Loxley, Ala. and ended April 30. Some blooms will appear in May through October in southern Alabama.

Fruit: Drupelike pome, ¼" to ⅜" diameter, 1 to 2 seeded berry. Summer fruit color Yellow-Green Group 144A ripens to Greyed-Purple Group 187A in the fall and persists as Black Group 202A attractively through the winter.

Culture: Grows well in a wide range of conditions and tolerates sun to part shade. Grows in nearly any soil type, from moist to very dry and sand to clay. Responds well to mulching and medium applications of fertilizer; prefers ph 6 to 7. Very little pruning is needed. Adaptable to containers and above ground planters. Ideal for coastal regions and warmer parts of the Piedmont. Tolerates wind and salt spray. Propagated with semi-hardwood cuttings in late spring through the summer.

I claim:

1. A new and unique variety of *Raphiolepis indica* plant named *Raphiolepis indica* 'Conor' as herein shown and described, is characterized by its dense and mounding growth habit, slow growth rate, thick leathery upturned leaves with unique revolute margins, bronze new growth and fragrant semi-double pink flowers; the landscape value of this plant is increased by the improved cold hardiness and resistance to leaf spot and fireblight as well as its tolerance of heat, drought, wind, salt, insects, and soil type.

* * * * *